United States Patent
Wall, Jr.

(10) Patent No.: US 12,296,149 B1
(45) Date of Patent: May 13, 2025

(54) SYRINGE ACTUATING CLIPS

(71) Applicant: Simeon Wall, Jr., Shreveport, LA (US)

(72) Inventor: Simeon Wall, Jr., Shreveport, LA (US)

( * ) Notice: Subject to any disclaimer, the term of this patent is extended or adjusted under 35 U.S.C. 154(b) by 234 days.

(21) Appl. No.: 17/486,220

(22) Filed: Sep. 27, 2021

(51) Int. Cl.
*A61M 5/31* (2006.01)

(52) U.S. Cl.
CPC ..... *A61M 5/3137* (2013.01); *A61M 2205/586* (2013.01)

(58) Field of Classification Search
CPC .......... A61M 5/3137; A61M 2205/586; A61M 2005/3139; A61M 5/3148
See application file for complete search history.

(56) References Cited

U.S. PATENT DOCUMENTS

| | | | |
|---|---|---|---|
| 3,040,744 A | 6/1962 | Hoggard | |
| 4,364,388 A | 12/1982 | Sech | |
| 4,594,073 A | 6/1986 | Sting | |
| 4,687,472 A | 8/1987 | Gross | |
| 4,737,151 A | 4/1988 | Clement et al. | |
| 5,115,816 A | 5/1992 | Lee | |
| 5,830,152 A | 11/1998 | Tao | |
| 6,197,006 B1 | 3/2001 | Wiklund | |
| 6,719,735 B1 | 4/2004 | Gammon | |
| 6,939,329 B1 | 9/2005 | Verkaart | |
| 7,118,556 B2 | 10/2006 | Nerney | |
| 9,067,023 B2 * | 6/2015 | Bertocci | A61M 5/3148 |
| 9,724,479 B2 | 8/2017 | Sutkin et al. | |
| 10,987,469 B2 | 4/2021 | Fojtik | |
| 2012/0041388 A1 | 2/2012 | Blomquist | |
| 2012/0059347 A1 * | 3/2012 | Freed | A61M 5/3129 604/218 |
| 2014/0018770 A1 | 1/2014 | Sutkin | |
| 2014/0350518 A1 | 11/2014 | Franklin et al. | |
| 2015/0328408 A1 | 11/2015 | Evans et al. | |
| 2016/0144125 A1 | 5/2016 | Franklin et al. | |

* cited by examiner

*Primary Examiner* — Bradley J Osinski
(74) *Attorney, Agent, or Firm* — R. Keith Harrison

(57) ABSTRACT

A syringe actuating clip configured for attachment to a medical syringe having a syringe barrel, a syringe plunger slidable in the syringe barrel and a thumb flange on the syringe plunger may include an elongated clip shaft having a first shaft end and a second shaft end. A syringe attachment head may include a syringe attachment head frame on the clip shaft at the first shaft end. The syringe attachment head frame may be disposed at a head angle with respect to the clip shaft. At least one head flange may be disposed adjacent and spaced-apart to the syringe attachment head frame. Accordingly, the syringe attachment head frame and the head flange of the syringe attachment head may be suitably sized and configured to receive and securely engage the thumb flange on the syringe plunger therebetween as the clip shaft extends adjacent to the syringe barrel. Medical syringe and syringe actuating clips are also disclosed.

22 Claims, 10 Drawing Sheets

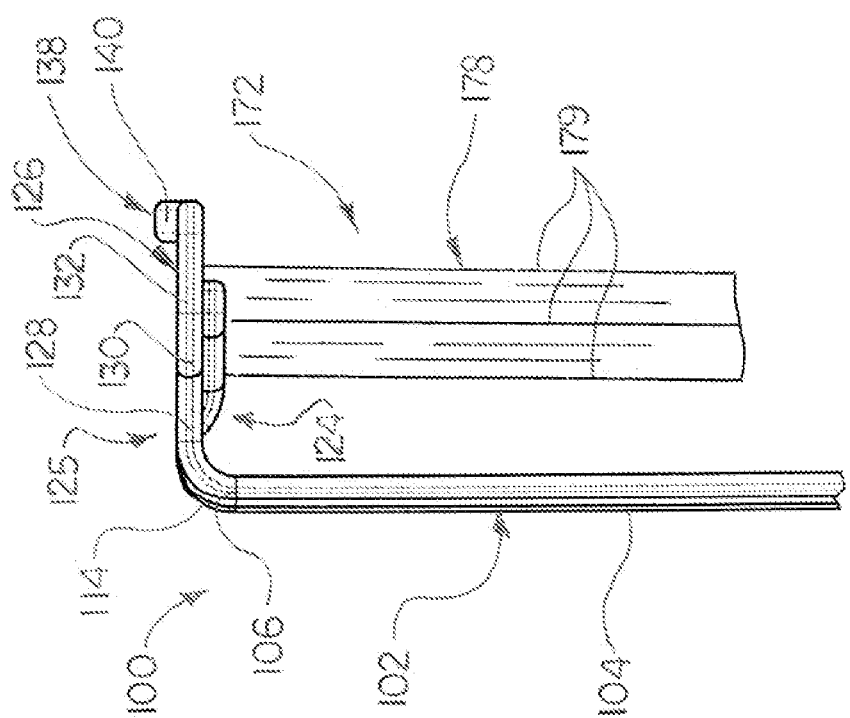

SYRINGE ACTUATING CLIPS

FIELD

Illustrative embodiments of the disclosure generally relate to medical syringes. More particularly, illustrative embodiments of the disclosure relate to syringe actuating clips which can be attached to a syringe plunger on a medical syringe to enable a syringe operator to ergonomically actuate the syringe with one hand while providing the operator with enhanced or precise control over ejection of selected quantities or volumes of medicament from the syringe.

SUMMARY

Illustrative embodiments of the disclosure are generally directed to syringe actuating clips configured for attachment to a medical syringe having a syringe barrel, a syringe plunger slidable in the syringe barrel and a thumb flange on the syringe plunger. An illustrative embodiment of the syringe actuating clips may include an elongated clip shaft having a first shaft end and a second shaft end. A syringe attachment head may include a syringe attachment head frame on the clip shaft at the first shaft end. The syringe attachment head frame may be disposed at a head angle with respect to the clip shaft. At least one head flange of the syringe attachment head may be disposed adjacent and spaced-apart to the syringe attachment head frame. Accordingly, the syringe attachment head frame and the head flange of the syringe attachment head may be suitably sized and configured to receive and securely engage the thumb flange on the syringe plunger therebetween as the clip shaft extends adjacent to the syringe barrel.

Illustrative embodiments of the disclosure are further generally directed to medical syringe and syringe actuating clips for ergonomically actuating a medical syringe with enhanced or precise control over ejection of selected quantities or volumes of medicament from the syringe. An illustrative embodiment of the medical syringe and syringe actuating clips may include a medical syringe including a syringe barrel, a syringe plunger slidable in the syringe barrel and a thumb flange on the syringe plunger. A syringe actuating clip may include an elongated clip shaft having a first shaft end and a second shaft end. A syringe attachment head of the syringe actuating clip may include a syringe attachment head frame on the clip shaft at the first shaft end. The syringe attachment head frame may be disposed at a head angle with respect to the clip shaft. At least one head flange may be disposed adjacent and spaced-apart to the syringe attachment head frame. The syringe attachment head frame and the head flange of the syringe attachment head may receive and securely engage the thumb flange on the syringe plunger therebetween as the clip shaft extends adjacent to the syringe barrel.

BRIEF DESCRIPTION OF THE DRAWINGS

Illustrative embodiments of the disclosure will now be described, by way of example, with reference to the accompanying drawings, in which:

FIG. 5 is an enlarged right-side view of the syringe actuating clip, with the syringe attachment head on the syringe actuating clip attached to the thumb flange on the syringe plunger.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear". "right", "front", "vertical", "horizontal", and derivatives thereof shall relate to the invention as oriented in FIG.

1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 7:
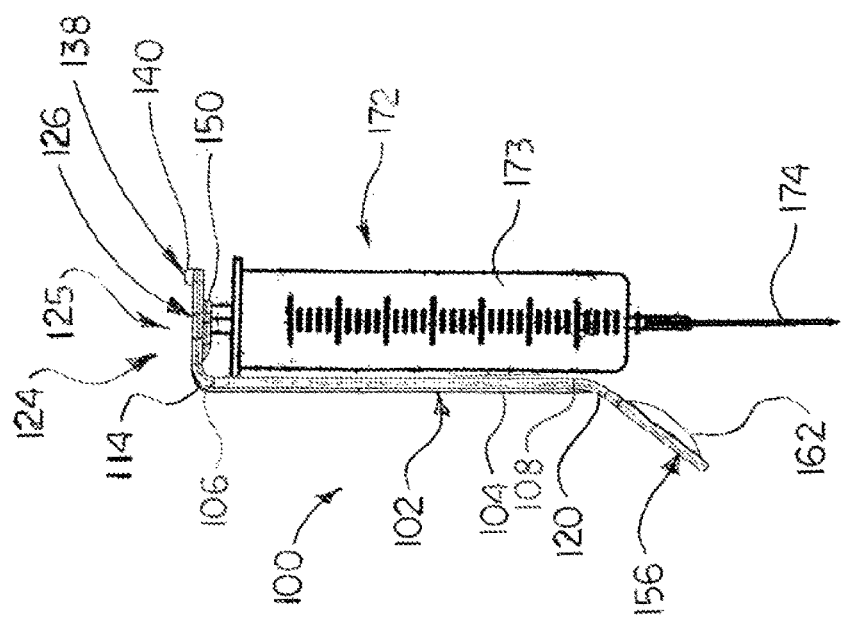
FIG. 7 is a right-side view of the syringe actuating clip attached to the syringe plunger, with the syringe plunger retracted into the syringe barrel.
Figure 6:
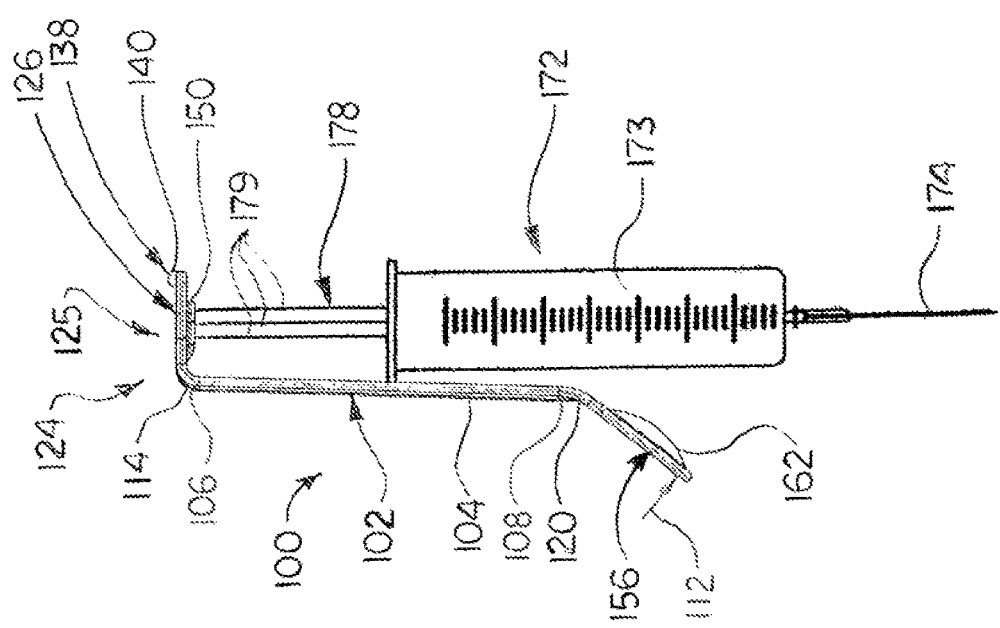
FIG. 6 is a right-side view of the syringe actuating clip attached to the syringe plunger, with the syringe plunger extended from the syringe barrel of the medical syringe preparatory to retracting the syringe plunger into the syringe barrel by application of manual force to the syringe actuating clip in typical application thereof.

Referring initially to FIGS. 1-7 of the drawings, an illustrative embodiment of the syringe actuating clips is generally indicated by reference numeral 100. As illustrated in FIGS. 6 and 7 and will be hereinafter described, the syringe actuating clip 100 may be suitably configured for attachment to a medical syringe 172 to enable a syringe operator (not illustrated) to ergonomically actuate the syringe 172 typically with one hand while providing the operator with enhanced or precise control over ejection of selected quantities or volumes of medicament from the syringe 172. The medical syringe 172 may be conventional, typically having a graduated syringe barrel 173; a cannula 174 extending from the syringe barrel 173; a syringe plunger 178 slidable in the syringe barrel 173; and a thumb flange 180 on the syringe plunger 178.

As illustrated in FIGS. 1-5, the syringe actuating clip 100 may include an elongated clip shaft 102. The clip shaft 102 may include an elongated, straight main shaft segment 104 having a proximal shaft end 106 and a distal shaft end 108. A curved proximal shaft segment 114 may extend from the first shaft end 106 of the main shaft segment 104. In some embodiments, a curved distal shaft segment 120 may extend from the distal shaft end 108 of the main shaft segment 104, typically for purposes which will be hereinafter described.

Figure 2:
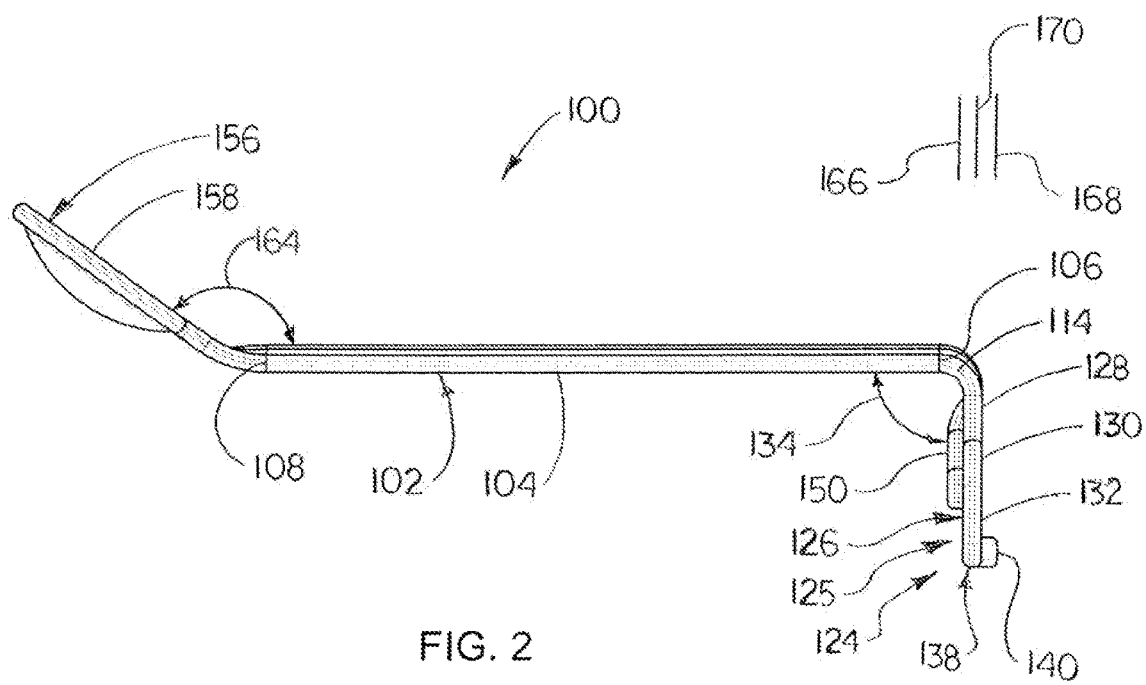
FIG. 2 is a right-side view of the syringe actuating clip illustrated in FIG. 1.
Figure 3:
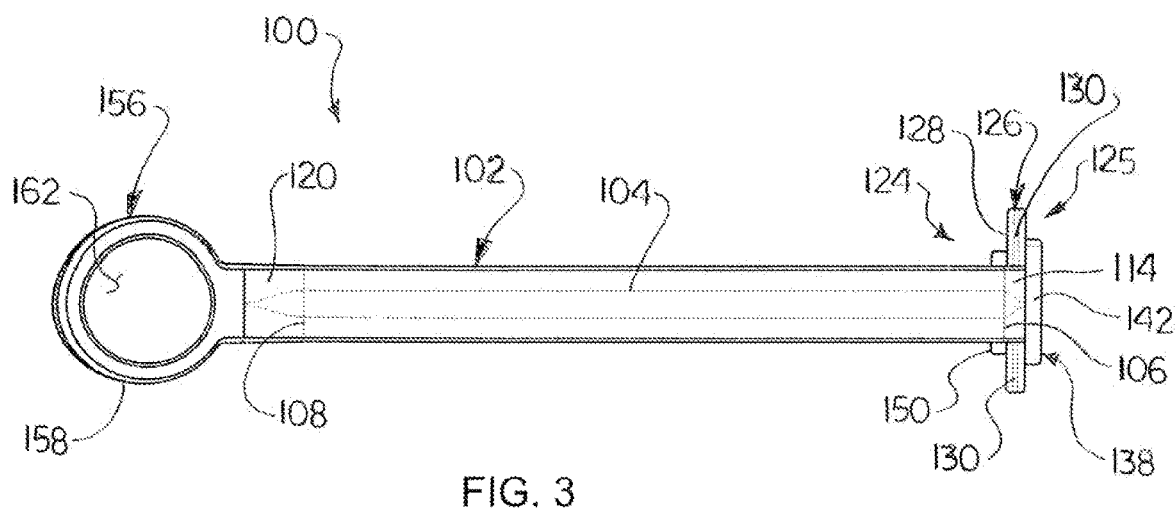
FIG. 3 is a front view of the syringe actuating clip illustrated in FIG. 1.

A syringe attachment head 124 may include a syringe attachment head frame 125 which extends from the proximal shaft segment 114 of the clip shaft 102. As illustrated in FIG. 2, the syringe attachment head frame 125 of the syringe attachment head 124 may be disposed at a head angle 134 with respect to the clip shaft 102. In some embodiments, the head angle 134 may be an obtuse angle, as illustrated, to deploy the clip shaft 102 outwardly from the syringe barrel 173 in attachment of the syringe actuating clip 100 to the medical syringe 172, as illustrated in FIGS. 6 and 7, typically as will be hereinafter described. Accordingly, as illustrated in FIGS. 6 and 7, in attachment of the syringe attachment head 124 to the thumb flange 180 on the syringe plunger 178 of the medical syringe 172, the syringe attachment head 124 may be configured to support the clip shaft 102 in a cantilevered configuration from the first shaft end 106 in attachment of the syringe attachment head 124 to the syringe plunger 178 of the medical syringe 172. The clip shaft 102 may thus remain unattached and unconnected to the syringe barrel 173 of the medical syringe 172 in attachment of the syringe actuating clip 100 to the medical syringe 172.

The syringe attachment head frame 125 of the syringe attachment head 124 may include a pair of spaced-apart syringe attachment arms 126. A terminal head member 138 may extend between the syringe attachment arms 126. A frame opening 146 may be formed by and between the syringe attachment arms 126 and the terminal head member 138. In some embodiments, the syringe attachment arms 126 of the syringe attachment head frame 125 may include a pair of spaced-apart base arm segments 128. A pair of spaced-apart middle arm segments 130 may extend and curve outwardly from the respective base arm segments 128. A pair of spaced-apart, straight terminal arm segments 132 may extend from the respective middle arm segments 130. The terminal head member 138 of the syringe attachment head frame 125 may extend between the terminal arm segments 132 of the syringe attachment arms 126.

In some embodiments, the terminal head member 138 of the syringe attachment head frame 125 may include a pair of curved end member segments 140 which may extend from the respective terminal arm segments 132 of the syringe attachment arms 126. A straight middle member segment 142 may extend between the curved end member segments 140. The middle member segment 142 may be disposed in the terminal head member plane 168 (FIG. 2), with the end member segments 140 extending from the respective syringe attachment arms 126 in the syringe attachment arm plane 170 to the middle member segment 142 in the terminal head member plane 168. In some embodiments, the middle member segment 142 of the terminal head member 138 may be elongated and continuous, as illustrated.

Figure 1:
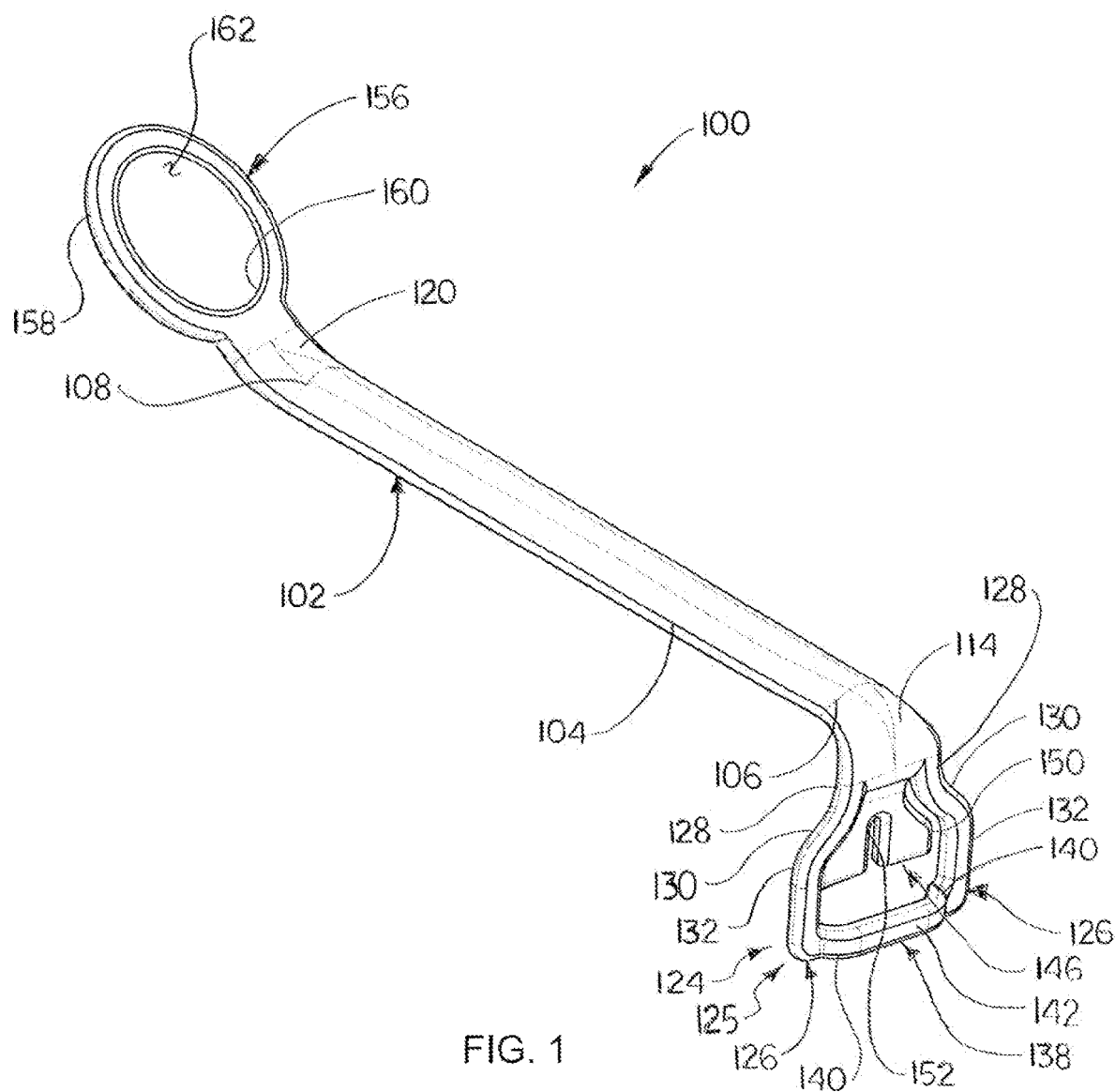
FIG. 1 is a top perspective view of an illustrative embodiment of the syringe actuating clips.

The syringe attachment head 124 may further include at least one head flange 150 which may be disposed adjacent and spaced-apart to the frame opening 146 and the syringe attachment head frame 125. As illustrated in FIG. 1, in some embodiments, the head flange 150 may extend from the proximal shaft segment 114 of the clip shaft 102. As illustrated in FIG. 2, the head flange 150 of the syringe attachment head 124 may be disposed in a head flange plane 166. The terminal head member 138 of the syringe attachment head frame 125 may be disposed in a terminal head member plane 168 which is parallel to the head flange plane 166. The syringe attachment arms 126 of the syringe attachment head frame 125 may be disposed in a syringe attachment arm plane 170 which is parallel to and between the head flange plane 166 and the terminal head member plane 168. Accordingly, in typical attachment of the syringe actuating clip 100 to the medical syringe 172, as illustrated in FIGS. 4-7 and will be hereinafter described, the frame opening 146 (FIG. 1) of the syringe attachment head frame 125 may be suitably sized and configured to receive the thumb flange 180 on the syringe plunger 178 of the medical syringe 172. The syringe attachment head frame 125 and the head flange 150 of the syringe attachment head 124 may be configured to securely engage the thumb flange 180 on the syringe plunger 178 as the clip shaft 102 extends adjacent to the syringe barrel 173.

As illustrated in FIG. 1, in some embodiments, an elongated flange slot 152 may extend into the head flange 150 of the syringe attachment head 124. The flange slot 152 may be suitably sired and configured to receive a plunger flange 179 on the syringe plunger 178 of the medical syringe 172 in attachment of the syringe actuating clip 100 to the medical syringe 172, typically as % ill be hereinafter described.

In some embodiments, a clip handle 156 may extend from the clip shall 102 at the distal shaft end 108. The clip handle 156 may include a clip handle frame 158. A handle opening 160 may extend through the clip handle frame 158. A concave handle wall 162 may extend from the clip handle frame 158 adjacent to the handle opening 160. Accordingly, in typical application of the syringe actuating clip 100, the operator of the medical syringe 172 may extend a finger (not illustrated) through the handle opening 160 to facilitate manual actuation of the syringe actuating clip 100.

As illustrated in FIG. 2, the clip handle 156 may be disposed at a handle angle 164 with respect to the clip shaft 102. In some embodiments, the handle angle 164 may be an obtuse angle, as illustrated. In other embodiments, the handle angle 164 may be a right angle or an acute angle.

As illustrated in FIGS. 4-7, in typical application, the syringe actuating clip 100 may be attached to the medical syringe 172 to enable a syringe operator (not illustrated) to ergonomically actuate the syringe 172 typically with one hand while providing the operator with enhanced or precise control over ejection of selected quantities or volumes of medicament from the syringe 172. Accordingly, a selected quantity or volume of a liquid medicament (not illustrated) may initially be placed in the syringe barrel 173 of the medical syringe 172 typically by retracting the syringe plunger 178 in the syringe barrel 173, placing the syringe cannula 174 into a vial or other container (not illustrated) which contains the medicament and extending the syringe plunger 178 from the syringe barrel 173 to draw the medicament from the container, through the syringe cannula 174 into the syringe barrel 173.

Figure 4:
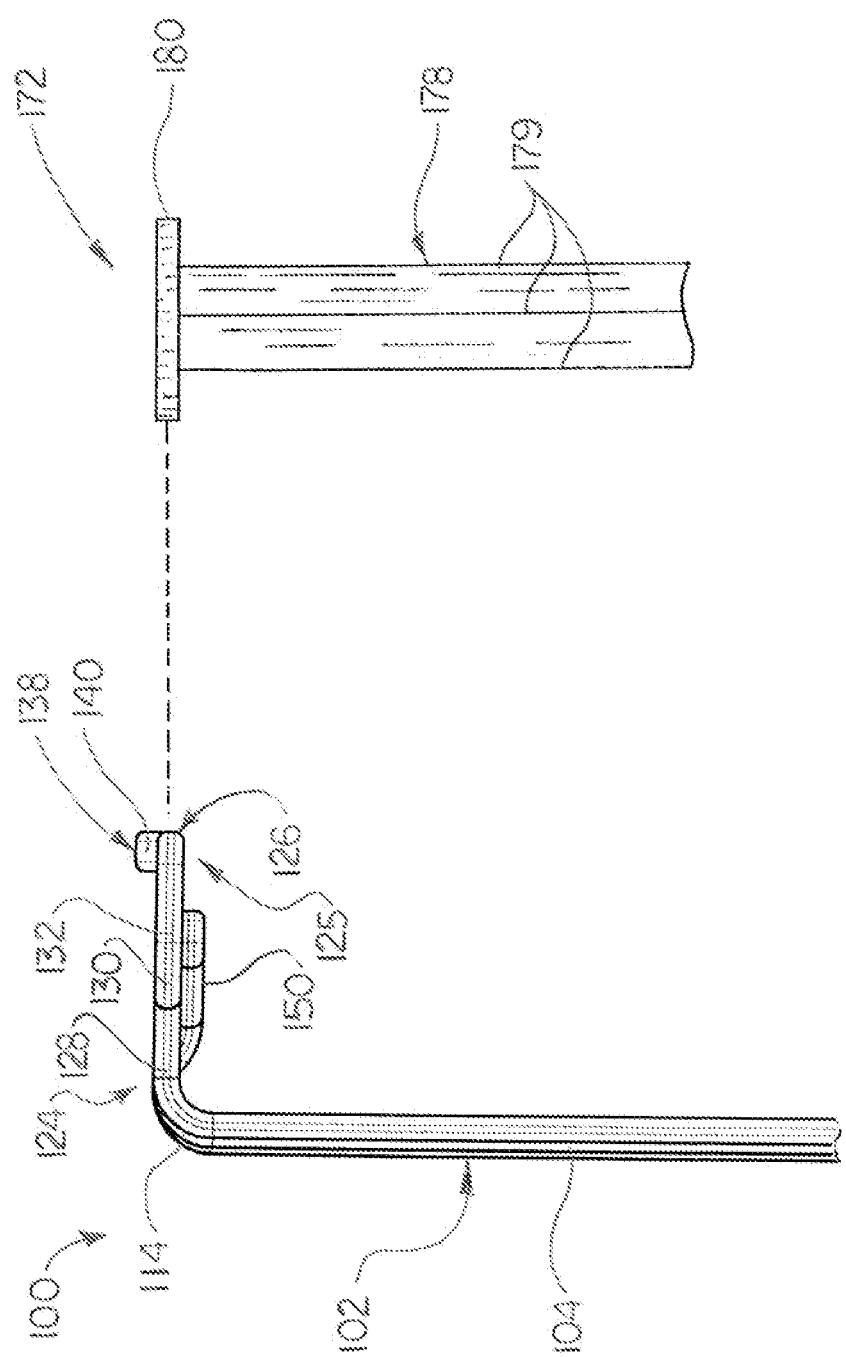
FIG. 4 is an enlarged right-side view of the syringe actuating clip, more particularly illustrating typical attachment of a syringe attachment head on the syringe actuating clip to a thumb flange on a syringe plunger of a medical syringe in typical application of the syringe actuating clip.

As illustrated in FIG. 4, the syringe attachment arms 126 on the syringe attachment head frame 125 of the syringe attachment head 124 may initially be positioned in alignment or registration with the thumb flange 180 on the syringe plunger 179 of the medical syringe 172. As illustrated in FIG. 5, the thumb flange 180 may then be inserted into the frame opening 146 (FIG. 1) of the syringe attachment frame 125 as the thumb flange 180 initially passes under or beneath the middle member segment 142 of the terminal head member 138 and then between the terminal arm segments 132 of the syringe attachment arms 126. One of the plunger flanges 179 on the syringe plunger 178 may simultaneously insert into the flange slot 152 (FIG. 1) in the head flange 150 as the head flange 150 engages the lower surface of the thumb flange 180. Therefore, the syringe attachment head frame 125 and the head flange 150 of the syringe attachment head 124 may securely engage the thumb flange 180 on the syringe plunger 178 therebetween as the clip shaft 102 extends adjacent to the syringe barrel 173.

The syringe operator may grasp and hold the medical syringe 172 typically with one hand with the fingers extending around and engaging the clip shaft 102 of the syringe actuating clip 100. In some applications, the thumb, index finger or little finger on the grasping hand of the syringe operator may insert through the handle opening 160 and engage the concave handle wall 162 of the clip handle 156.

The syringe operator may next insert the syringe cannula 174 into or through the skin of a patient (not illustrated) to the target area in or beneath the skin. As illustrated in FIG. 6, the syringe operator may then apply pressure 112 typically to the clip handle 156 of the syringe actuating clip 100 such that the syringe attachment head 124 applies linear pressure to the thumb flange 180 which causes the syringe plunger 178 to retract into the syringe barrel 173 and expel the medicament from the syringe barrel 173 through the syringe cannula 174 into the patient. It will be appreciated by those skilled in the art that the syringe actuating clip 100 enables the syringe operator to ergonomically actuate the medical syringe 172 with one hand while providing the syringe operator with enhanced or precise control over ejection of selected quantities or volumes of the medicament from the syringe 172.

After the contents of the syringe barrel 173 are exhausted, the syringe cannula 174 may be removed from the patient. The syringe attachment head 124 of the syringe actuating clip 100 may be detached from the thumb flange 180 and the medical syringe 172 discarded. In some applications, the syringe actuating clip 100 may be attached to the thumb flange 180 on the syringe plunger 178 of another medical syringe 172 and reused in like manner.

Figure 8:
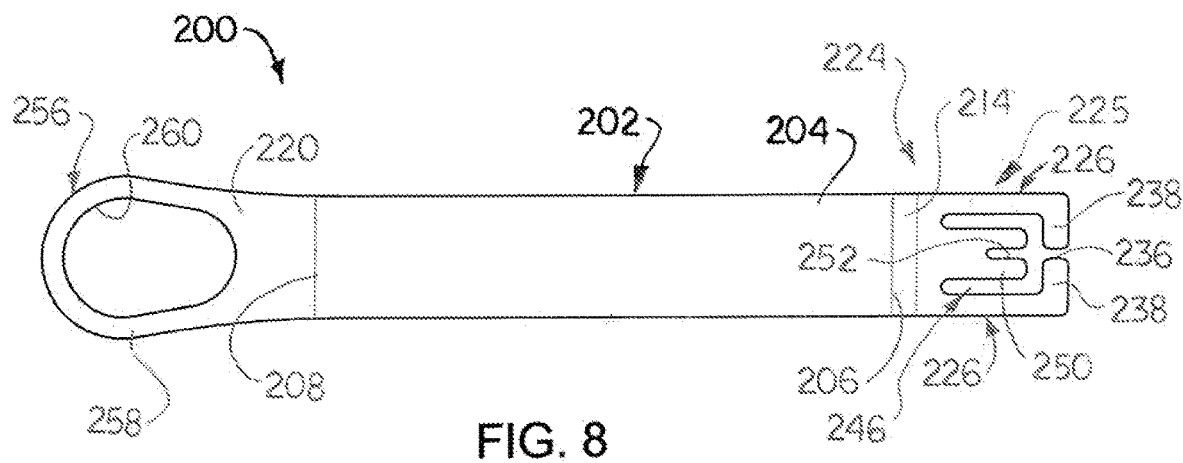
FIG. 8 is a top view of an alternative illustrative embodiment of the syringe actuating clips, with the syringe attachment head, the clip shaft and the clip handle of the syringe actuating clip disposed flat in a common plane for illustrative purposes.
Figure 9:
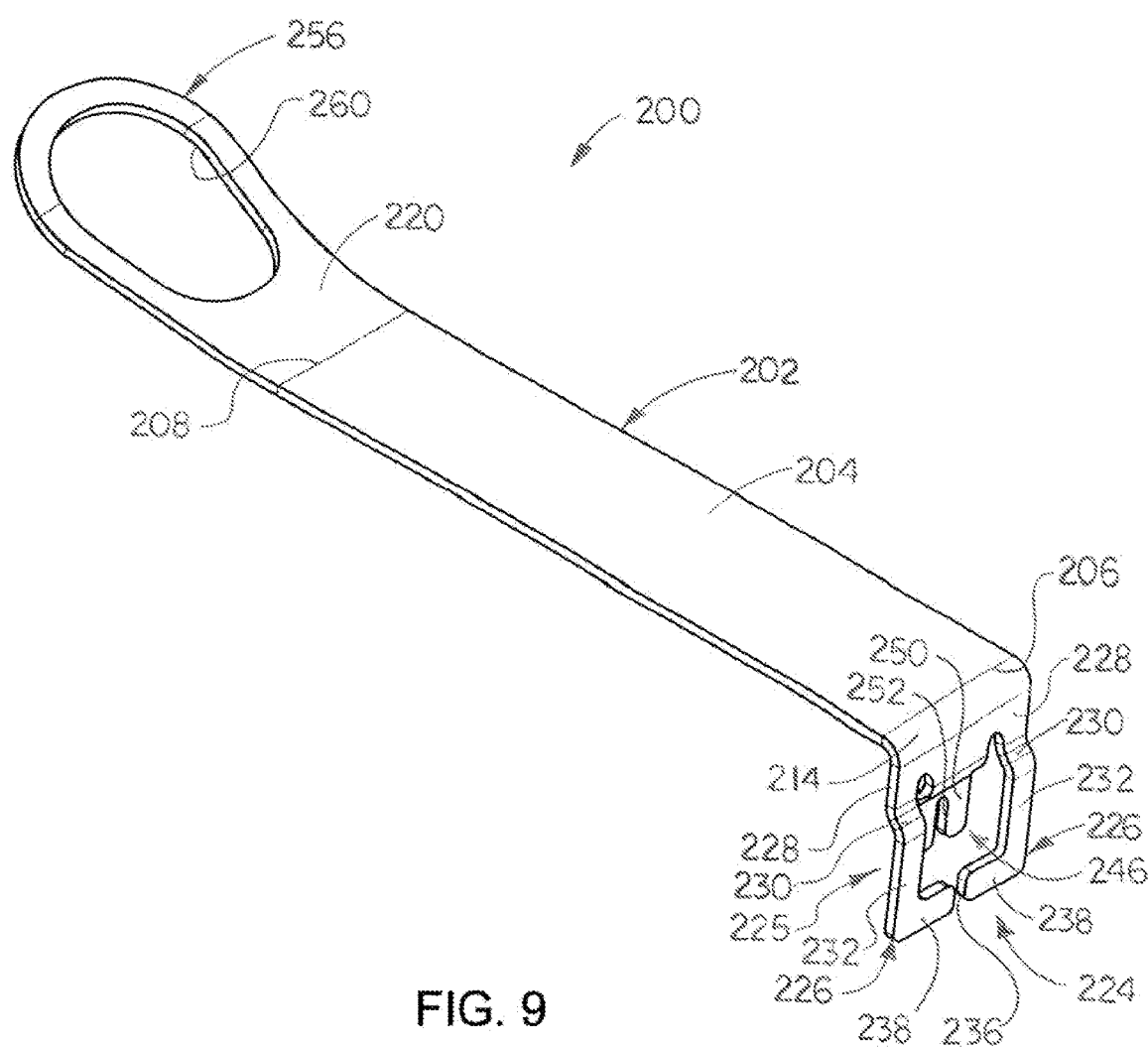
FIG. 9 is a top perspective view of the illustrative syringe actuating clip illustrated in FIG. 8.
Figure 10:
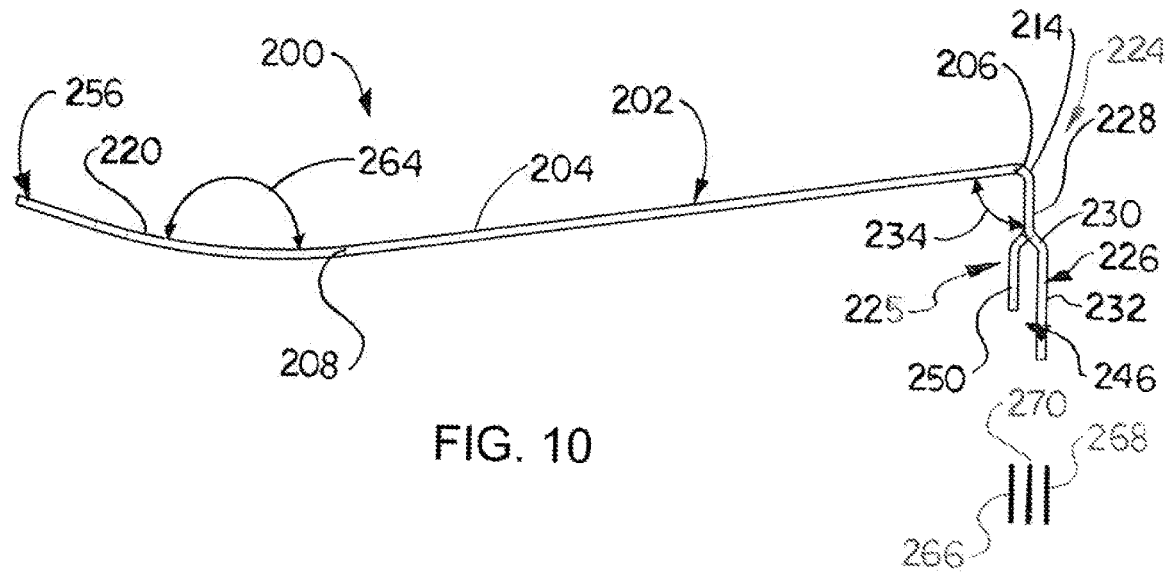
FIG. 10 is a right-side view of the illustrative syringe actuating clip illustrated in FIG. 8.
Figure 11:
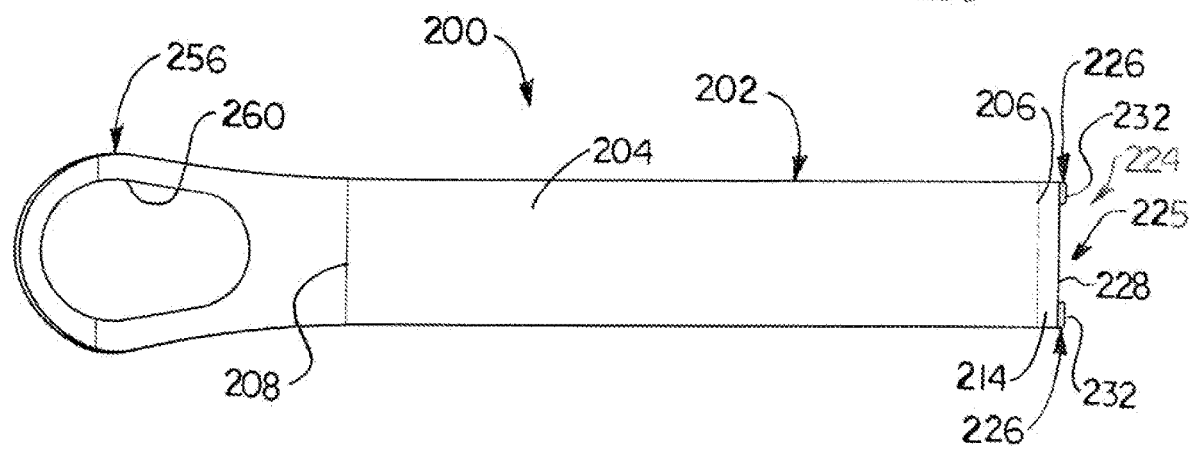
FIG. 11 is a top view of the illustrative syringe actuating clip illustrated in FIG. 8.

Referring next to FIGS. 8-15 of the drawings, an alternative illustrative embodiment of the syringe actuating clips is generally indicated by reference numeral 200. In the syringe actuating clip 200, elements which are analogous to the respective elements of the syringe actuating clip 100 that was heretofore described with respect to FIGS. 1-7 are designated by the same respective numerals in the 201-299 series in FIGS. 8-15. As illustrated in FIG. 10, the head angle 234 of the syringe actuating clip 200 may be disposed at a right or acute angle with respect to the clip shaft 202. The middle arm segment 230 may curve or extend at an angle from the base arm segment 228 on each syringe attachment arm 226 of the syringe attachment frame 225. Accordingly, the base arm segment 228 may be disposed in the arm plane 270 and the terminal arm segment 232 may be disposed in the head member plane 268. The frame opening 246 may be disposed between the head flange 250 and the terminal arm segments 232 of the syringe attachment arms 226.

As illustrated in FIGS. 8 and 9, in some embodiments, a terminal head member notch 236 may be provided in the terminal head member 238 of the syringe attachment head frame 225. Accordingly, the terminal head member 238 may be elongated, discontinuous or interrupted as it extends between the terminal arm segments 232 of the syringe attachment arms 226.

Figure 12:
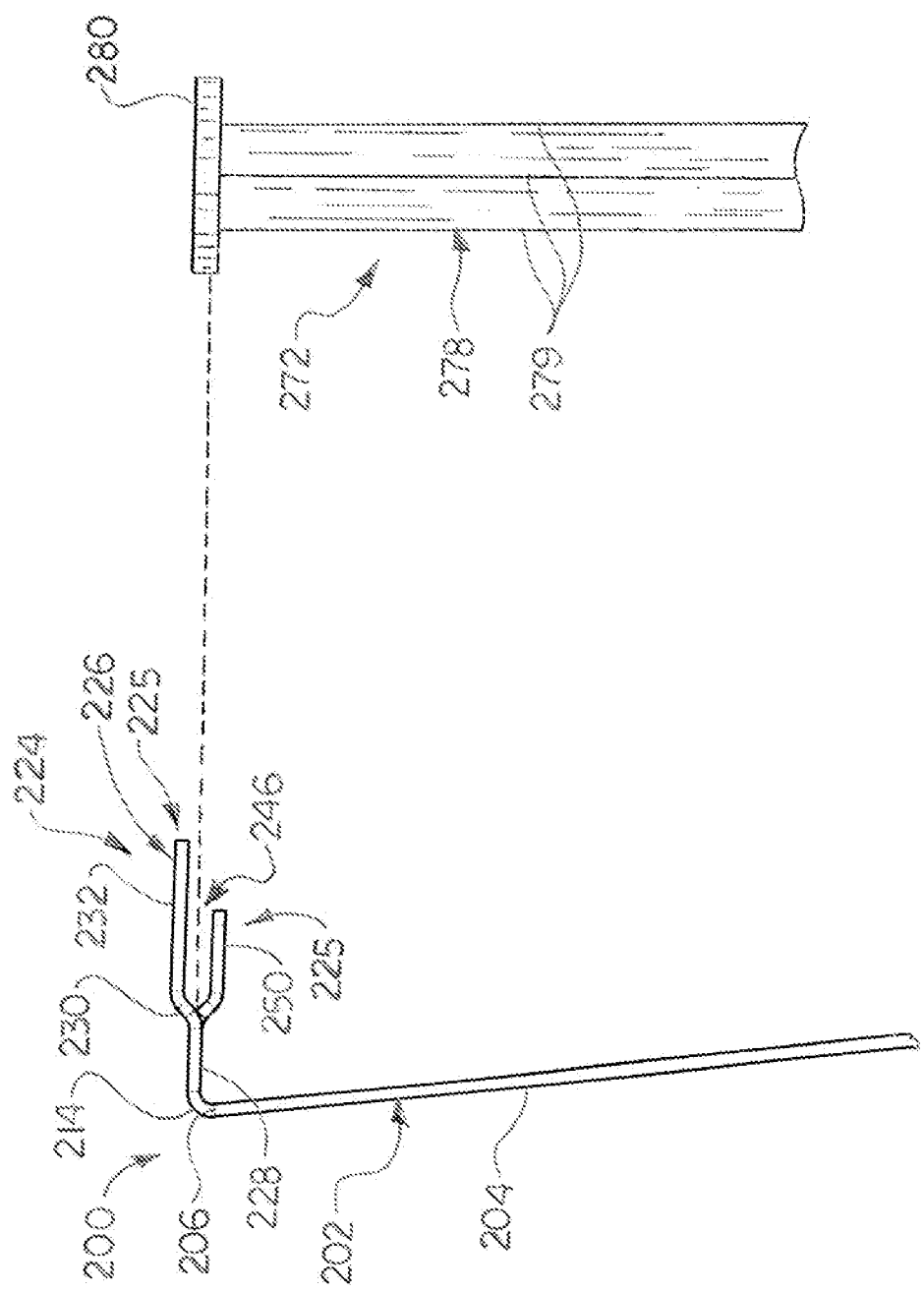
FIG. 12 is an enlarged right-side view of the syringe actuating clip illustrated in FIG. 8, more particularly illustrating typical attachment of a syringe attachment head on the syringe actuating clip to a thumb flange on a syringe plunger of a medical syringe in typical application of the syringe actuating clip.
Figure 13:
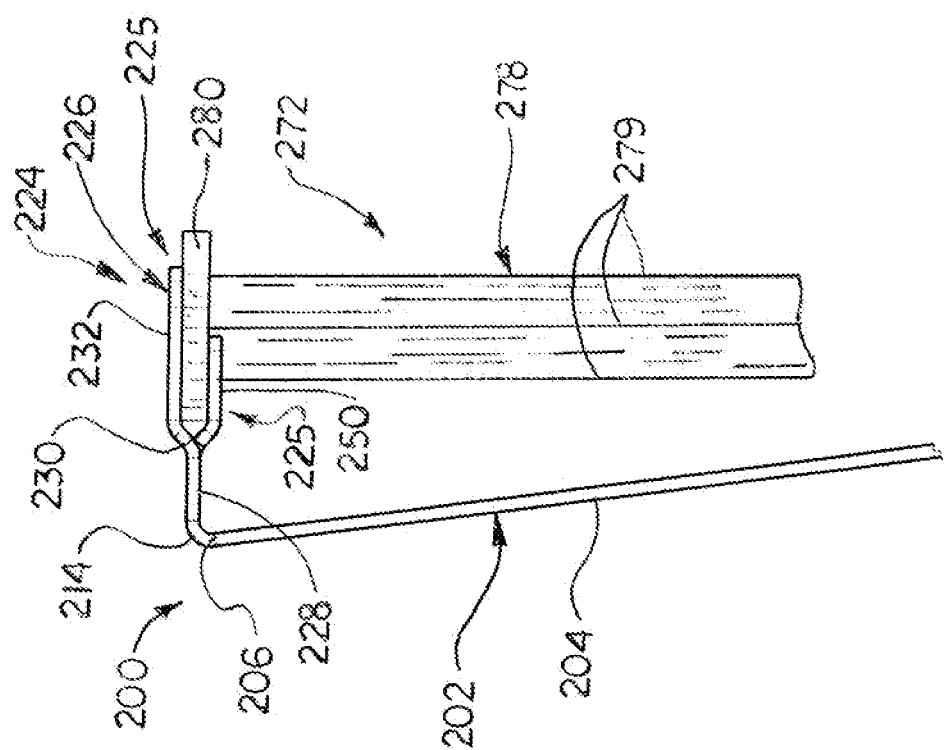
FIG. 13 is an enlarged right-side view of the syringe actuating clip illustrated in FIG. 8, with the syringe attachment head on the syringe actuating clip attached to the thumb flange on the syringe plunger.
Figure 15:
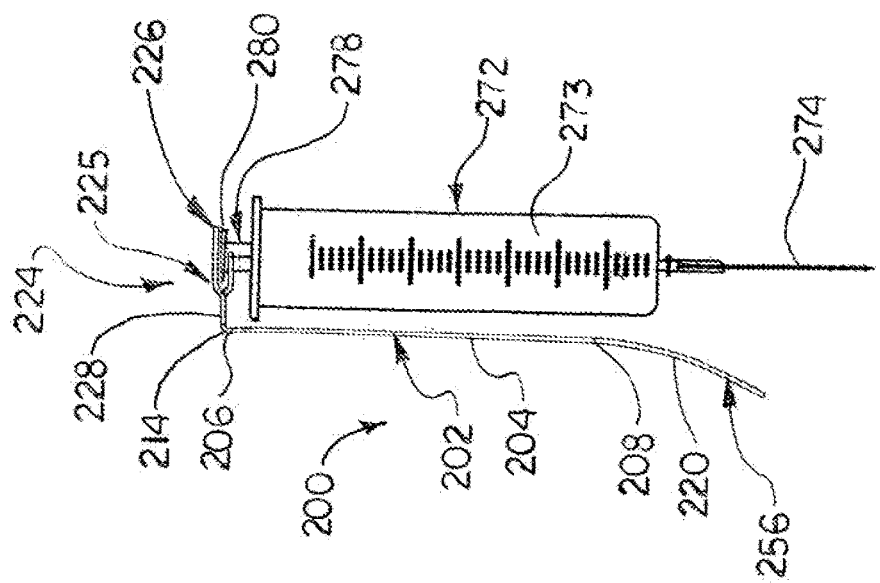
FIG. 15 is a right-side view of the syringe actuating clip illustrated in FIG. 8, attached to the syringe plunger, with the syringe plunger retracted into the syringe barrel.
Figure 14:
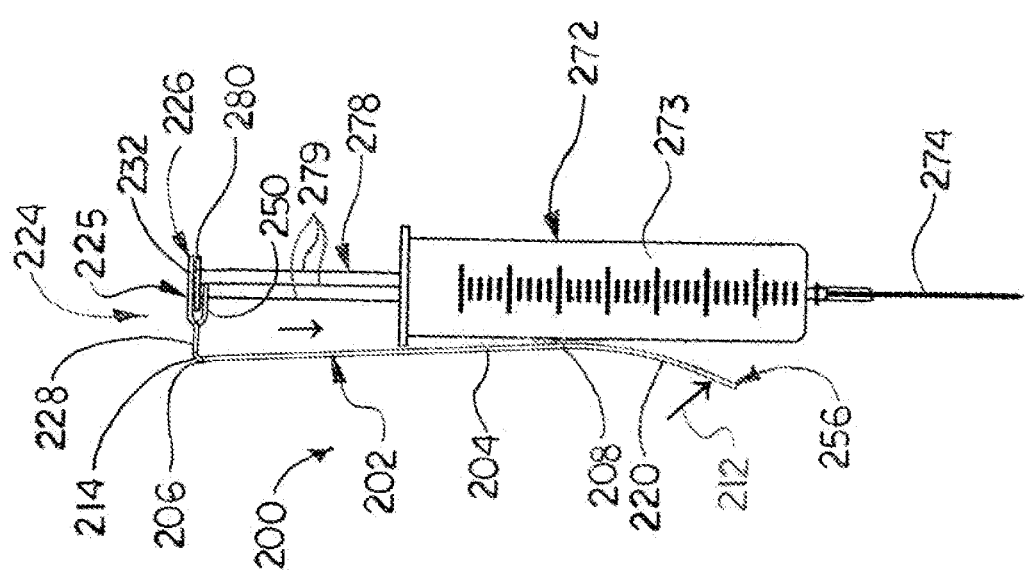
FIG. 14 is a right-side view of the syringe actuating clip illustrated in FIG. 8, attached to the syringe plunger, with the syringe plunger extended from the syringe barrel of the medical syringe preparatory to retracting the syringe plunger into the syringe barrel by application of manual force to the syringe actuating clip in typical application thereof.

As illustrated in FIGS. 12-15, application of the syringe actuating clip 200 may be as was heretofore described with respect to that of the syringe actuating clip 100 in FIGS. 4-7. Accordingly, as illustrated in FIG. 12, the syringe attachment arms 226 on the syringe attachment head frame 225 of the syringe attachment head 224 may initially be positioned in alignment or registration with the thumb flange 280 on the syringe plunger 278 of the medical syringe 272. The thumb flange 280 may then be inserted into the frame opening 246 (FIGS. 8 and 9) of the syringe attachment frame 225 as the thumb flange 280 initially passes under or beneath the terminal head member 238 and then between the terminal arm segments 232 of the syringe attachment arms 226. One of the plunger flanges 279 on the syringe plunger 278 may simultaneously insert into the flange slot 252 (FIGS. 1 and 2) in the head flange 250 as the head flange 250 engages the lower surface of the thumb flange 280. Therefore, the syringe attachment head frame 225 and the head flange 250 of the syringe attachment head 224 may securely engage the thumb flange 280 on the syringe plunger 278 as the clip shat 202 extends adjacent to the syringe barrel 273.

While certain illustrative embodiments of the disclosure have been described above, it will be recognized and understood that various modifications can be made to the embodiments and the appended claims are intended to cover all such modifications which may fall within the spirit and scope of the disclosure.

What is claimed is:

1. A syringe actuating clip configured for attachment to a medical syringe having a syringe barrel, a syringe plunger slidable in the syringe barrel and a thumb flange on the syringe plunger, the syringe actuating clip comprising:
   an elongated clip shaft having a first shaft end and a second shaft end;
   a syringe attachment head on the clip shaft at the first shaft end, the syringe attachment head configured to support the clip shaft in a cantilevered configuration from the first shaft end in attachment of the syringe attachment head to the syringe plunger of the medical syringe, the syringe attachment head including:

a syringe attachment head frame carried by the clip shaft at the first shaft end, the syringe attachment head frame disposed at an obtuse head angle with respect to the clip shaft for angular deployment of the clip shaft outwardly away from the syringe barrel at the obtuse head angle in attachment of the syringe actuating clip to the medical syringe; and at least one head flange disposed adjacent and spaced-apart to the syringe attachment head frame; and wherein the syringe attachment head frame and the at least one head flange of the syringe attachment head are suitably sized and configured to receive and securely engage the thumb flange on the syringe plunger therebetween as the clip shaft extends adjacent to and angles away from the syringe barrel at the obtuse head angle and the clip shaft is configured to remain unattached and unconnected to the syringe barrel of the medical syringe in attachment of the syringe actuating clip to the medical syringe.

2. The syringe actuating clip of claim 1 wherein the clip shaft comprises an elongated, straight main shaft segment and a curved shall segment extending from the first shaft end, and the syringe attachment head frame of the syringe attachment head extends from the curved shaft segment.

3. The syringe actuating clip of claim 1 further comprising a clip handle carried by the clip shaft at the second shaft end.

4. The syringe actuating clip of claim 3 wherein the clip handle comprises a clip handle frame and a handle opening extending through the clip handle frame.

5. The syringe actuating clip of claim 4 further comprising a concave handle wall extending from the clip handle frame adjacent to the handle opening.

6. The syringe actuating clip of claim 3 wherein the clip handle is disposed at a handle angle with respect to the clip shaft.

7. The syringe actuating clip of claim 1 wherein the syringe attachment head frame comprises a pair of spaced-apart syringe attachment arms.

8. The syringe actuating clip of claim 7 further comprising a terminal head member extending between the pair of spaced-apart syringe attachment arms.

9. A syringe actuating clip configured for attachment to a medical syringe having a syringe barrel, a syringe plunger slidable in the syringe barrel and a thumb flange on the syringe plunger, comprising:

an elongated clip shaft having a first shaft end and a second shaft end;

a syringe attachment head on the clip shaft at the first shaft end, the syringe attachment head configured to support the clip shaft in a cantilevered configuration from the first shaft end in attachment of the syringe attachment head to the syringe plunger of the medical syringe, the syringe attachment head including:

a syringe attachment head frame carried by the clip shaft at the first shaft end, the syringe attachment head frame disposed at a head angle to the clip shaft, the syringe attachment head frame disposed at an acute head angle with respect to the clip shaft for angular deployment of the clip shaft inwardly toward the syringe barrel in attachment of the syringe actuating clip to the medical syringe; and wherein the syringe attachment head frame and the at least one head flange of the syringe attachment head are configured to securely engage therebetween the thumb flange on the syringe plunger as the clip shaft extends adjacent to and angles toward the syringe barrel at the acute head angle and the clip shaft is configured to remain unattached and unconnected to the syringe barrel of the medical syringe in attachment of the syringe actuating clip to the medical syringe.

10. The syringe actuating clip of claim 9 wherein the clip shaft comprises an elongated, straight main shaft segment and a curved shaft segment extending from the first shaft end, and the syringe attachment head frame of the syringe attachment head extends from the curved shaft segment.

11. The syringe actuating clip of claim 9 further comprising a clip handle carried by the clip shaft at the second shaft end.

12. The syringe actuating clip of claim 11 wherein the clip handle comprises a clip handle frame and a handle opening extending through the clip handle frame.

13. The syringe actuating clip of claim 12 further comprising a concave handle wall extending from the clip handle frame adjacent to the handle opening.

14. The syringe actuating clip of claim 11 wherein the clip handle is disposed at a handle angle with respect to the clip shaft.

15. The syringe actuating clip of claim 9 further comprising g frame opening in the syringe attachment head frame, at least one head flange disposed adjacent and spaced-apart to the frame opening and an elongated flange slot extending into the at least one head flange of the syringe attachment head.

16. The syringe actuating clip of claim 9 wherein the syringe attachment head frame of the syringe attachment head comprises a pair of spaced-apart syringe attachment arms comprising a pair of spaced-apart base arm segments; a pair of spaced-apart middle arm segments extending from the pair of spaced-apart base arm segments, respectively; and a pair of straight, spaced-apart terminal arm segments extending from the pair of spaced-apart middle arm segments, respectively, and g terminal head member extending between the pair of straight, spaced-apart terminal arm segments.

17. The syringe actuating clip of claim 9:

wherein the clip shaft has an elongated main shaft segment with the first shaft end and the second shaft end, a curved first shaft segment extending from the first shaft end and a curved second shaft segment extending from the second shaft end, and the syringe attachment head includes:

a pair of spaced-apart syringe attachment arms having a pair of base arm segments, respectively, extending from the first shaft segment at the first shaft end of the main shaft segment;

a pair of middle arm segments extending and curving outwardly from the pair of base arm segments, respectively;

a pair of terminal arm segments extending from the pair of middle arm segments, respectively; and a terminal head member extending between the pair of spaced-apart syringe attachment arms, wherein the terminal head member is elongated, continuous and extends between the pair of terminal arm segments of the pair of spaced-apart syringe attachment arms; and further comprising a clip handle extending from the second shaft segment at the second shaft end of the main shaft segment, the clip handle including:

a clip handle frame;

a handle opening extending through the clip handle frame; and a concave handle wall extending from the clip handle frame adjacent to the handle opening.

18. The syringe actuating clip of claim 17 wherein the clip handle is disposed at a handle angle with respect to the clip shaft.

19. The syringe actuating clip of claim 9:
wherein the clip shaft has an elongated main shaft segment with the first shaft end and the second shaft end, a curved first shaft segment extending from the first shaft end and a curved second shaft segment extending from the second shaft end, and the syringe attachment head includes:
  a pair of spaced-apart syringe attachment arms having a pair of base arm segments, respectively, extending from the first shaft segment at the first shaft end of the main shaft segment;
  a pair of middle arm segments extending and curving outwardly from the pair of base arm segments, respectively;
  a pair of terminal arm segments extending from the pair of middle arm segments, respectively; and
  a terminal head member extending between the pair of spaced-apart syringe attachment arms, wherein the terminal head member is elongated, discontinuous or interrupted and extends between the pair of terminal arm segments, the terminal head member including a terminal head member notch; and
further comprising a clip handle extending from the second shaft segment at the second shaft end of the main shaft segment, the clip handle including:
  a clip handle frame; and
  a handle opening extending through the clip handle frame.

20. A medical syringe and syringe actuating clip for ergonomically actuating the syringe with enhanced or precise control over ejection of medicament from the syringe, comprising:
  a medical syringe including:
    a syringe barrel;
    a syringe plunger slidable in the syringe barrel; and
    a thumb flange on the syringe plunger; and
  a syringe actuating clip including:
    an elongated clip shaft having a first shaft end and a second shaft end; and
    a syringe attachment head on the clip shaft at the first shaft end, the syringe attachment head supporting the clip shaft on the syringe plunger of the medical syringe in a cantilevered configuration from the first shaft end, the syringe attachment head including:
      a syringe attachment head frame carried by the clip shaft at the first shaft end, the syringe attachment head frame disposed at a head angle with respect to the clip shaft; and
      at least one head flange disposed adjacent and spaced-apart to the syringe attachment head frame; and
    the syringe attachment head frame and the at least one head flange of the syringe attachment head receiving and securely engaging the thumb flange on the syringe plunger therebetween as the clip shaft extends adjacent to the syringe barrel and the clip shaft is unattached and unconnected to the syringe barrel of the medical syringe.

21. The medical syringe and syringe actuating clip of claim 20 wherein the head angle is an obtuse head angle.

22. The medical syringe and syringe actuating clip of claim 20 wherein the head angle is an acute head angle.

* * * * *